US008470146B2

(12) United States Patent
Betti et al.

(10) Patent No.: US 8,470,146 B2
(45) Date of Patent: Jun. 25, 2013

(54) CABLE INSERTION FOR CORROSION SENSORS

(75) Inventors: Raimondo Betti, Tenafly, NJ (US); Alan West, Tenafly, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 182 days.

(21) Appl. No.: 12/836,435

(22) Filed: Jul. 14, 2010

(65) Prior Publication Data

US 2011/0011751 A1 Jan. 20, 2011

Related U.S. Application Data

(60) Provisional application No. 61/225,917, filed on Jul. 15, 2009.

(51) Int. Cl.
*G01N 27/26* (2006.01)
(52) U.S. Cl.
USPC ............ 204/404; 205/775.5; 324/700; 73/86
(58) Field of Classification Search
USPC ............. 324/71.2, 693, 700; 205/775, 775.5, 205/776, 777; 204/404; 73/86
See application file for complete search history.

(56) References Cited

U.S. PATENT DOCUMENTS

| 4,367,651 | A | * | 1/1983 | Cameron et al. ............... 73/706 |
| 7,034,660 | B2 | | 4/2006 | Watters et al. |
| 2006/0162431 | A1 | | 7/2006 | Harris et al. |

FOREIGN PATENT DOCUMENTS

WO   WO 2009097645 A1 *   8/2009

* cited by examiner

*Primary Examiner* — Luan Van
*Assistant Examiner* — Maris R Kessel
(74) *Attorney, Agent, or Firm* — Evans & Molinelli PLLC; Eugene J. Molinelli

(57) ABSTRACT

A method and apparatus for sensing corrosion comprises a casing and a counter-electrode. The casing is made of material that is substantively incompressible at pressures on wires within a structural cable. The casing has a thickness that is not greater than typical interstitial spaces between wires of the structural cable and has a length on an order of a radius of the structural cable. The counter-electrode exchanges electrons with ions of an electrolyte that corrodes the wires of the structural cable. The counter-electrode is embedded in the casing, is exposed to the electrolyte in a window of the casing, and is recessed to avoid contact with any wire of the structural cable when the sensor is deployed among the wires of the structural cable.

11 Claims, 8 Drawing Sheets

FIG. 2A
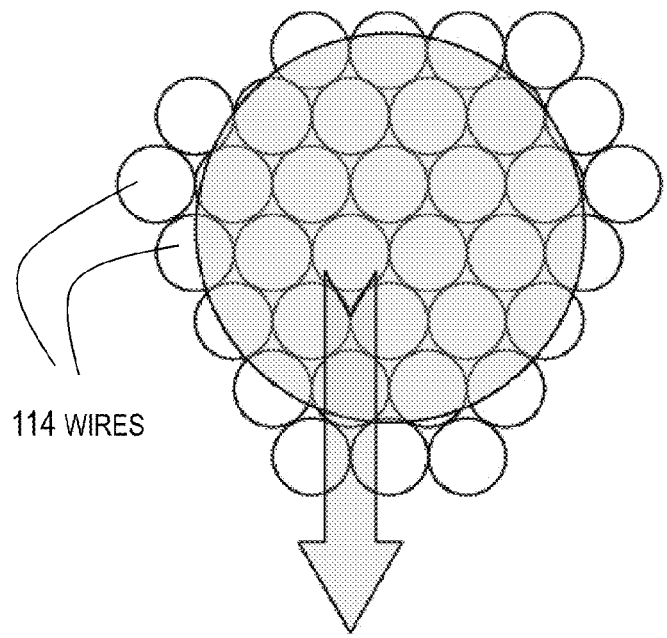
114 WIRES
FIG. 2B
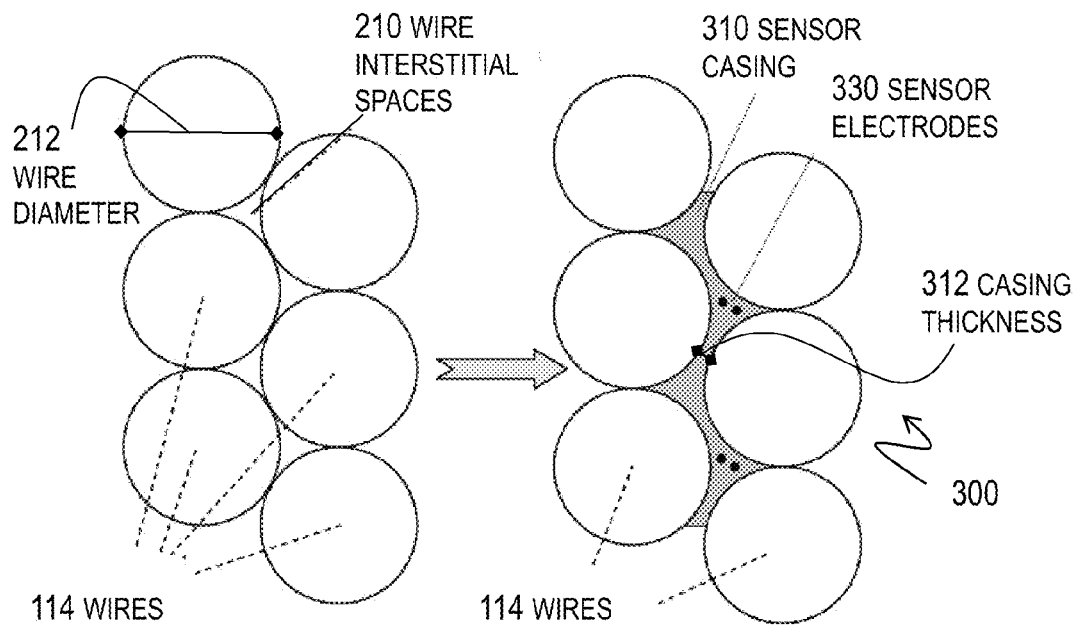
210 WIRE INTERSTITIAL SPACES
212 WIRE DIAMETER
114 WIRES
FIG. 3A
310 SENSOR CASING
330 SENSOR ELECTRODES
312 CASING THICKNESS
114 WIRES
300

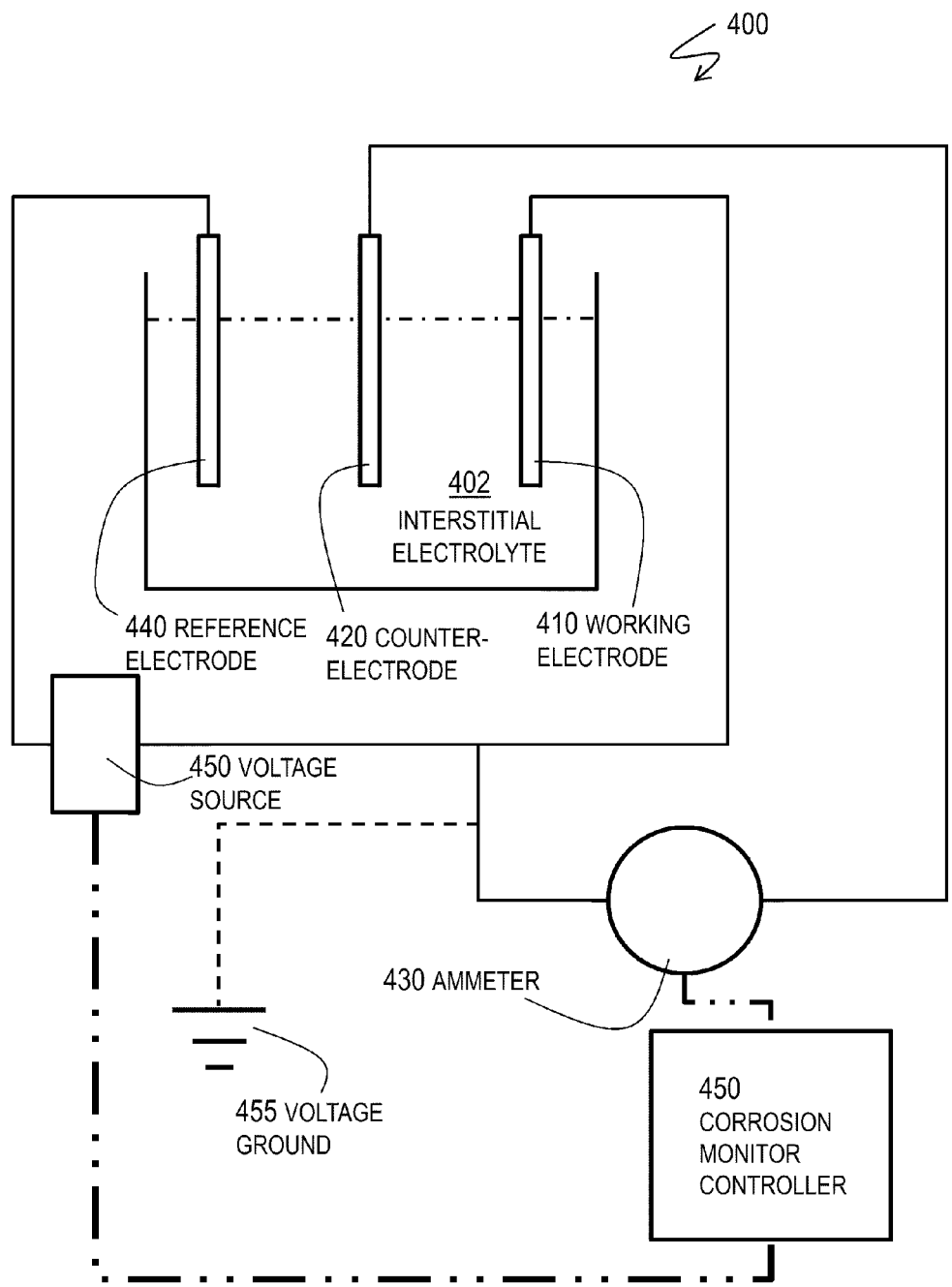

CABLE INSERTION FOR CORROSION SENSORS

CROSS-REFERENCE TO RELATED APPLICATIONS

This application claims benefit of Provisional Appln. 61/225,917, filed Jul. 15, 2009, the entire contents of which are hereby incorporated by reference as if fully set forth herein, under 35 U.S.C. §119(e).

BACKGROUND OF THE INVENTION

1. Field of the Invention

The present invention relates to corrosion sensors for cables, such as suspension bridge cables.

2. Description of the Related Art

A significant problem relevant to the infrastructures of a country, including the United States, is the ability to monitor the corrosion rates of cables used in suspension and cable-stay bridges. Corrosion of main cables of suspension bridges is the main and most challenging problem that bridge owners face today. Failure of a main cable of a suspension bridge corresponds to the failure of the entire bridge. Replacement of a cable is a very costly operation, with a cost around $200 million per bridge. Unfortunately, cable deterioration is happening and there is no means to reliably assess it and control it. Many of these monumental bridges (usually cable suspension bridges are quite large) have already passed their expected service life and, because of the importance they have gained in our infrastructure system (such as in New York City), they must be kept fully operational. Because there is not a reliable sensor that can be directly used in such applications, bridge cable maintenance is done in a very crude fashion, by opening the cable at those locations that are suspected to be corroded and pouring oil products into the cable.

SOME EXAMPLE EMBODIMENTS

Techniques are provided for sensing corrosion and include a casing and a counter-electrode. The casing is made of material that is substantively incompressible at pressures on wires within a structural cable. The casing has a thickness that is not greater than typical interstitial spaces between wires of the structural cable and has a length on an order of a radius of the structural cable. The counter-electrode exchanges electrons with ions of an electrolyte that corrodes the wires of the structural cable. The counter-electrode is embedded in the casing, is exposed to the electrolyte in a window of the casing, and is recessed to avoid contact with any wire of the structural cable when the sensor is deployed among the wires of the structural cable.

In some embodiments a method includes inserting a casing with counter-electrode as described above in a cable when the cable is opened, as during inspection.

BRIEF DESCRIPTION OF THE DRAWINGS

The present invention is illustrated by way of example, and not by way of limitation, in the figures of the accompanying drawings and in which like reference numerals refer to similar elements and in which:

FIG. 2A and FIG. 2B are cross-sectional diagrams that illustrate wires in a structural cable;

FIG. 3A is a cross-sectional diagram that illustrates a corrosion sensor, according to an embodiment;

FIG. 4 is a block diagram that illustrates a corrosion rate measurement analogous to a corrosion rate measurement used according to an embodiment;

DETAILED DESCRIPTION

Figure 1A:
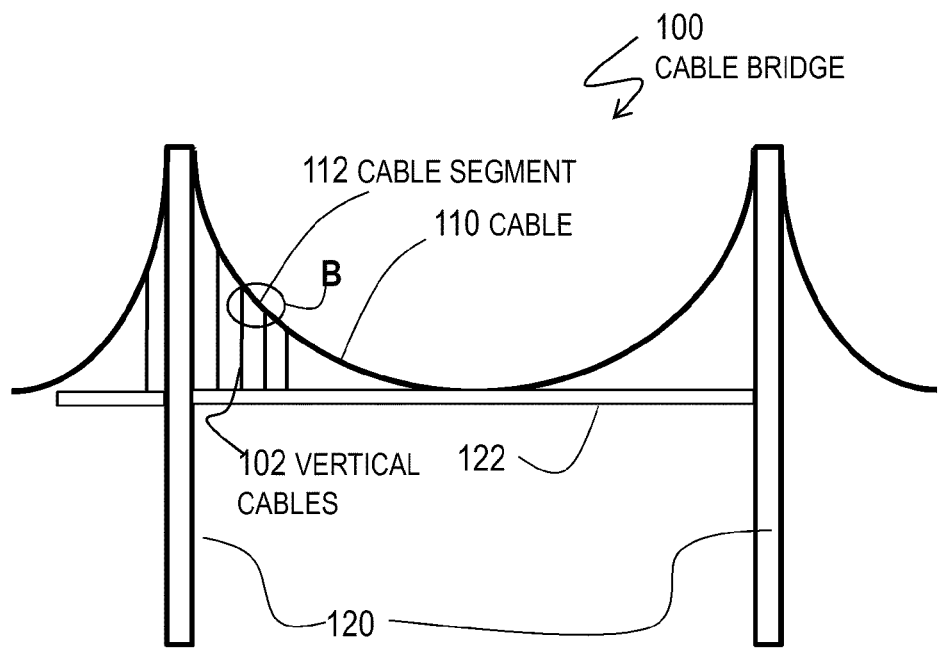
FIG. 1A and FIG. 1B are block diagrams that illustrate a structural cable used in a suspension bridge.

A method and apparatus are described for inserting corrosion sensors in a structural cable. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of suspension bridges, such as the George Washington Bridge connecting Manhattan, N.Y. with Fort Lee, N.J. However, the invention is not limited to this context. In other embodiments, sensors are inserted into structural cables constructed of multiple wires in other structures, such as guide wires for towers and support cables for elevators, counterweights and balconies.

Major suspension bridges in the U.S. are required to undergo visual inspection along twenty-foot segments at least once every two years. For example, the George Washington Bridge is to undergo a more extensive inspection of the entire length of the suspension cables at a cost of approximately $20 million. The visual inspection occurs by opening the protective wrapping around the cable, inserting wedges to open the cable all the way to its middle, and subsequent cataloguing of damaged and broken wires (often caused by corrosion). At the time of this inspection, it would be possible to insert sensors to monitor, for example, the corrosion rate of the wires at interior positions of the cable. However, because of the enormous forces involved and the constricted geometry between individual wires of the cable, there are presently no sensor technologies that can be successfully inserted into the cable without an anticipation of failure during the closure of the cable.

There are, however, sensors for corrosion monitoring of structures such as storage tanks, where the corrosion occurs primarily at the surface and the sensor can be placed on a relatively flat surface. These sensors are based on a variety of mechanisms, some of which can be used for corrosion in structural cables. For example, corrosion sensors that are based on electrochemical measurements have been extensively demonstrated in the past, and they are suitable for monitoring corrosion in structural cables. These sensors involve monitoring a current through an electrolyte that contacts the structural element. One problem is that such sensors are configured as probes or surface mounted devices that do not function well when inserted among the wires of a structural cable.

According to various embodiments, a corrosion sensor is devised with a sensor casing that exposes measuring electrodes to the electrolyte that causes corrosion in the restricted geometries and high pressures of deployed structural cables without contacting those electrodes against the structural cable. In some of these embodiments, the structural cable functions as a working electrode that completes a circuit across the electrolyte with a counter-electrode embedded in the sensor casing. In other embodiments, a surrogate electrode, with a corrosion rate having a known relationship to the corrosion rate of the structural cable, functions as the working electrode.

Figure 1B:
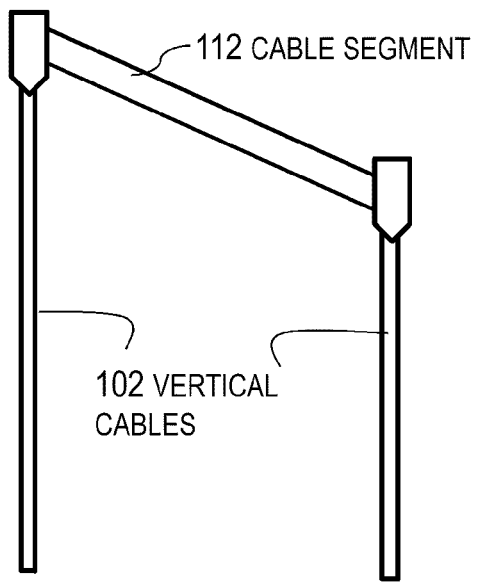

FIG. 1A and FIG. 1B are block diagrams that illustrate a structural cable 110 used in a suspension bridge 100. The structural cable 110 is suspended from two piers 120 and is connected to, and supports, a roadway 122 by multiple vertical cables 102. A section of the structural cable 110 between adjacent vertical cables 102 is called a cable segment 112.

For example, in a suspension bridge, the cable segments are about 20 feet long. The cable is made up of between about 7000 and 20,000 steel wires, each coated with zinc metal, which often forms on its surface a layer of zinc oxide. The wires are about five (5) millimeters (mm) in diameter (1 mm=$10^{-3}$ meters). The cable is about 18 to 40 inches in diameter. The cable itself is then coated with zinc paste, wrapped by a wrapping wire or rubber tape, and then painted.

Figure 1C:
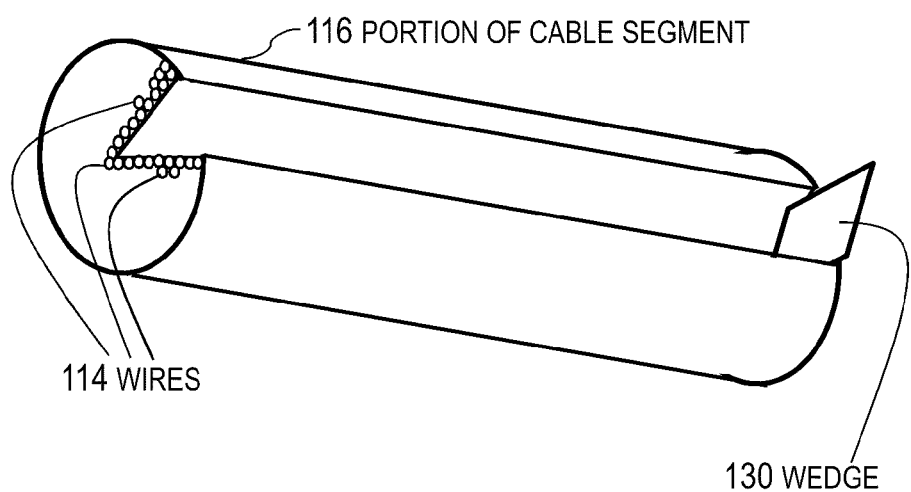
FIG. 1C is a block diagram that illustrates a cable segment opened for inspection using a wedge.

FIG. 1C is a block diagram that illustrates a portion 116 of a cable segment 112 opened for inspection using a wedge 130. FIG. 1C also indicates that the cable of portion 116 is made of a large number of individual wires 114, only some of which are depicted.

The inspection typically notes four degrees of wear: 1] the wires look new with intact zinc coating; 2] the zinc is missing in places, exposing steel; 3] the zinc is gone and rust is showing on the steel wires; and 4] the steel wires are rusted, pitted or broken. Typically, the wedge is inserted at 8 angles, roughly equally spaced around the circumference of the structural cable. Even so, only about 2% of the wires are inspected in the process.

FIG. 2A and FIG. 2B are cross-sectional diagrams that illustrate wires 114 in a structural cable 110. As depicted in FIG. 2B, the wire interstitial spaces 210 are a small fraction of the wire diameter 212. For a wire diameter of 5 mm, the interstitial spaces are about a couple of millimeters across at a maximum dimension. Electrolyte, such as salt water, in these interstitial spaces 210 leads to corrosion of the wires 114. An electrolyte is a medium in which ions are free to migrate, and thus is capable of conducting electricity.

FIG. 3A is a cross-sectional diagram that illustrates a corrosion sensor 300, according to an embodiment. Although wires 114 are shown for reference, they are not part of the corrosion sensor 300. The corrosion sensor 300 includes a thin casing 310, as viewed in this cross section, with a casing thickness 312 on the order of or small compared to the interstitial spaces, e.g., about 1 mm compared to interstitial spaces of 2 mm, and small compared to the diameter (e.g., 5 mm) of the wires 114. Embedded in the casing 310, out of contact with wires 114, are one or more sensor electrodes, e.g. the two sensor electrodes 330 depicted in FIG. 3A.

Figure 3B:
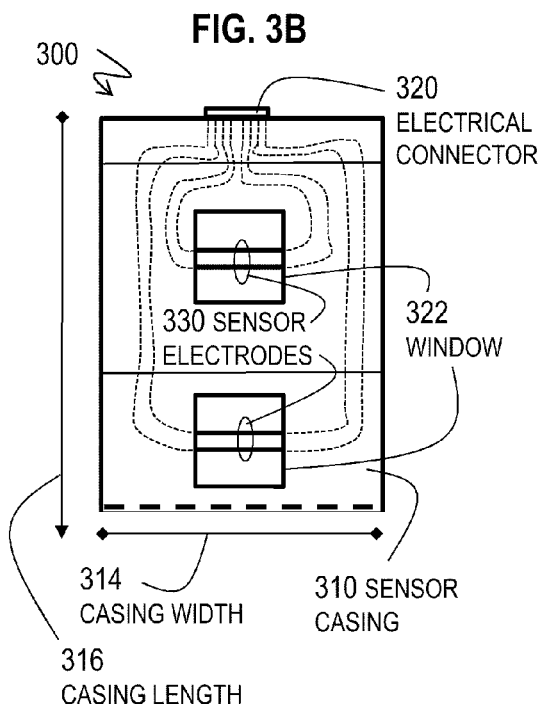
FIG. 3B is an elevation block diagram and FIG. 3C is a perspective diagram that illustrates a corrosion sensor, according to an embodiment.
Figure 3C:
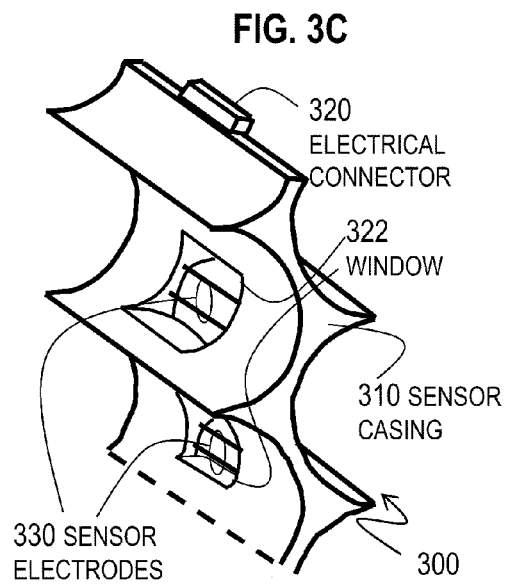

FIG. 3B is an elevation block diagram and FIG. 3C is a perspective diagram that illustrates a corrosion sensor 300, according to an embodiment. FIG. 3B depicts the sensor casing 310, with the sensor electrodes 330 exposed in windows 322. The electrodes 330 are recessed in the window 322 to keep from contacting any wires 114 in the cable, when the sensor 300 is deployed among the wires 114 in the cable 110. Each electrode of the sensor electrodes 330 is electrically connected to a separate, electrically insolated, pair of pegs in an electrical connector 320 at one end of the casing (called the "top" of the casing for convenience), as indicated by dashed lines. The casing width 314, in the longitudinal direction of the wires, is sufficient to keep the wires from compressing the casing and making contact with any of the sensor electrodes 330 exposed in the window 322. These pressures are expected to be about 2000 pounds per square inch (psi). The casing length 316 is sufficient to expose the sensor electrodes in a window 322 to at least one interstitial space. In the illustrated embodiment, the casing length 316 is long enough to expose the sensor electrodes in at least two windows 322. In some embodiments, the casing length 316 is a significant fraction (e.g., 90% to 100%) of the cable radius (e.g., 18 to 40 inches). In an example embodiment, the dimensions of the casing are 20 cm long, 3 cm wide and 0.3-0.4 cm thick. In various embodiments, the windows are square or rectangular with dimensions in a range from about 0.3 cm to about 1 cm.

In various embodiments, the casing 310 for the sensors are made of one of the different hard rubber materials available. Hard rubber is basically a plastic in which the matrix is a resinous material mixed with a polymerizing or curing agent and with fillers. In some embodiments, these fillers are high-strength organic fibers such as caoutchouc-type fibers. Because it is formed under heat and pressure to practically any form, hard rubber is particularly suitable for the sensor casing 310, since it can be molded to the scalloped shape of several 5-mm diameter semicircles to reproduce the wire distribution. Once the hard rubber has gone through the molding process with heat and pressure, hard rubber cannot be returned to its original state (thermosetting plastics).

Many of the hard rubber materials available today are made with Styrene-butadiene rubber. These are obtained by emulsion polymerization of butadiene and styrene in varying ratios (the most common ratio is 78:22). The usual range of Shore A hardness is between 50-90, with a percent elongation of 450-500%. Its Glass transition temperature is about −55° C. while its usual range of temperature is −40° C. to 100° C. The major use of such hard rubber is in tires and tire products, flooring, shoe products, sponge and molded goods. The hardness for the casing 314 is measured on the Shore D scale, which is several orders of magnitude higher than the Shore A scale used for conventional rubbers and elastomers. According to some embodiments, the casing is made of hard rubber that compresses less than about ten percent under pressures up to about 2000 pounds per square inch (psi), e.g., that shows a compressive strain of about 0.1 under a uniform compressive stress of about 2000 psi.

Corrosion of metal wires in the cable is due to an electrolyte that invades the interstitial spaces. The electrolyte is from rain, condensation from fog, mist, spray and other wetting sources. Because the outer coating of the bridge is imperfect, water (containing salts and other constituents) enters and travels throughout the cable in the interstitial spaces.

When the electrodes 330 are exposed to the electrolyte in the wire interstitial spaces 210, the rate of corrosion can be determined. Any set of two or three or more electrodes may be used. For example, as is well known in the art, corrosion rate can be determined based on a measurement of linear polarization resistance between a counter-electrode and a working electrode. A current or voltage can be measured or applied between the two pegs associated with an electrode to make the determination of corrosion rate, using any of the methods known in the art, and described in more detail below.

FIG. 3C, shows the sensor of FIG. 3B in perspective. As can be seen, the electrodes 330 are recessed from the lateral surface of the sensor casing 310. The sensor casing 310 includes multiple lips that are each shaped to fit into each of the wire interstitial spaces 210.

Figure 3D:
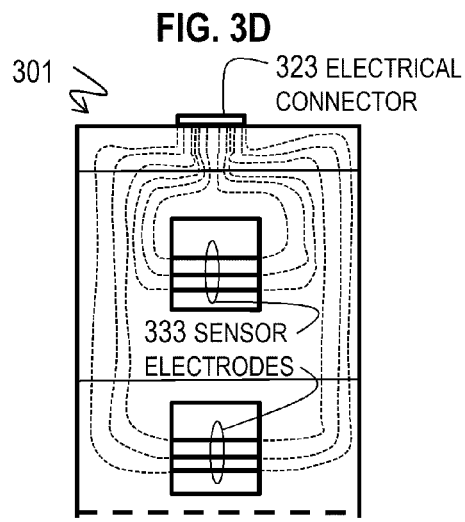
FIG. 3D is an elevation block diagram and FIG. 3E is a perspective diagram that illustrates a corrosion sensor, according to another embodiment.
Figure 3E:
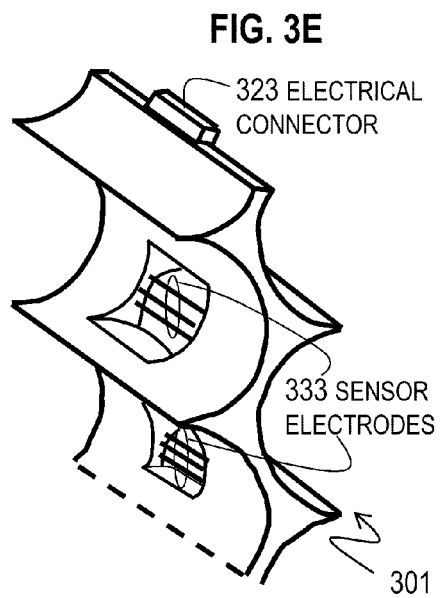

FIG. 3D is an elevation block diagram and FIG. 3E is a perspective diagram that illustrates a corrosion sensor 301, according to another embodiment, with three sensor electrodes 333 exposed in the windows and connected to pairs of pegs in connector 323.

FIG. 4 is a block diagram that illustrates a corrosion rate measurement 400 analogous to a corrosion rate measurement used according to an embodiment. The measurement includes three electrodes immersed in the interstitial electrolyte 402, including a working electrode 410, a counter-electrode 420, and a reference electrode 440. In some embodiments, the working electrode is grounded (indicated by the dashed line to ground 455). A current is measured between the working electrode 410, the electrolyte 402 and the counter-electrode 420 using ammeter 430. The reference electrode 440 is kept at a predetermined voltage relative to the working electrode 410 by voltage source 450. A corrosion monitor controller 450 controls the voltage source 450 and determines the corrosion rate based on the ammeter 430 measurements, as indicated by the dashed-double-dotted line.

Corrosion rate determination using multiple electrodes, including linear polarization resistance measurements, using three electrodes are described in Jones, D. A., *Principles and prevention of corrosion,* Macmillan Pub. Co., Maxwell Macmillan Canada, Maxwell Macmillan International Pub. Group, Toronto, 1992, (hereinafter Jones), the entire contents of which are herby incorporated by reference as if fully set forth herein for all purposes, except where the terminology conflicts with the use of terms defined herein.

The Auxiliary electrode of Jones is called the "counter-electrode" herein. The counter-electrode is a second electrode that is required to complete an electrochemical cell with a working electrode. The working electrode is the wire of the structural cable or a surrogate electrode made of either the same material or a material with corrosion rate having a known relationship with the corrosion rate of the material of the wire of the structural cable. If the working electrode is an anode, a cathodic reaction occurs on the counter-electrode. If the working electrode is a cathode, an anodic reaction occurs on the counter-electrode. Thus the counter-electrode is said to exchange electrons with ions of an electrolyte that corrodes the wires of the structural cable (the working electrode). The working electrode may be perturbed in either the cathodic or anodic direction to obtain a polarization mechanism. The reference electrode helps to ensure a more reliable measurement because it eliminates any resistances associated with the current flowing through the counter-electrode. Note that the ammeter measures the current flowing from the counter-electrode to ground when a surrogate is not used, because the bridge cable would be grounded. Steel or platinum may be used for the counter-electrode or the reference electrode, or both.

Thus, in some embodiments, the bridge cable, or a group of one or more wires therein, is used as the working electrode and the corrosion sensor only includes one electrode (a counter-electrode), or two electrodes (a counter-electrode and a reference electrode). In other embodiments, a surrogate electrode is used as the working electrode and the corrosion sensor includes two electrodes (a counter-electrode and the surrogate electrode) in sensor 300, or three electrodes (a counter-electrode and a reference electrode and the surrogate) in sensor 301.

Figure 5:
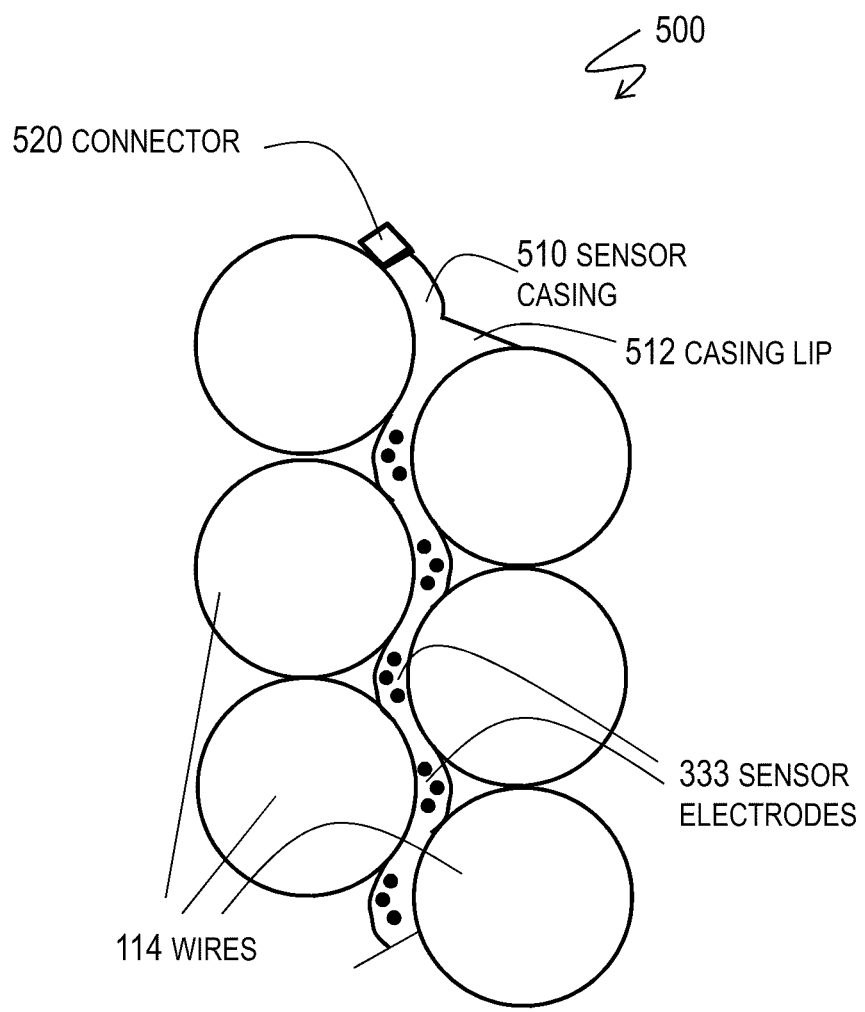
FIG. 5 is a cross-sectional diagram that illustrates a corrosion sensor, according to another embodiment.

FIG. 5 is a cross-sectional diagram that illustrates a corrosion sensor 500, according to another embodiment. Although wires 114 are shown for reference, wires 114 are not part of sensor 500. Sensor 500 includes casing 510, connector 520 and sensor electrodes 333. In this embodiment, the sensor casing 510 includes only one lip 512 to synchronize the spacing of the sensor electrodes, e.g. the three sensor electrodes 333, with the interstitial spaces between the wires 114. This spacing is a distance that is about an integer multiple of a radius of a wire in the structural cable. Otherwise, the sensor casing 510 is uniformly thin, e.g., about one (1) millimeter. The connector 520 is at the top. Windows (not shown) are along the width of the casing 510 to expose the electrodes 333 to the interstitial electrolyte, as described above.

Figure 6A:
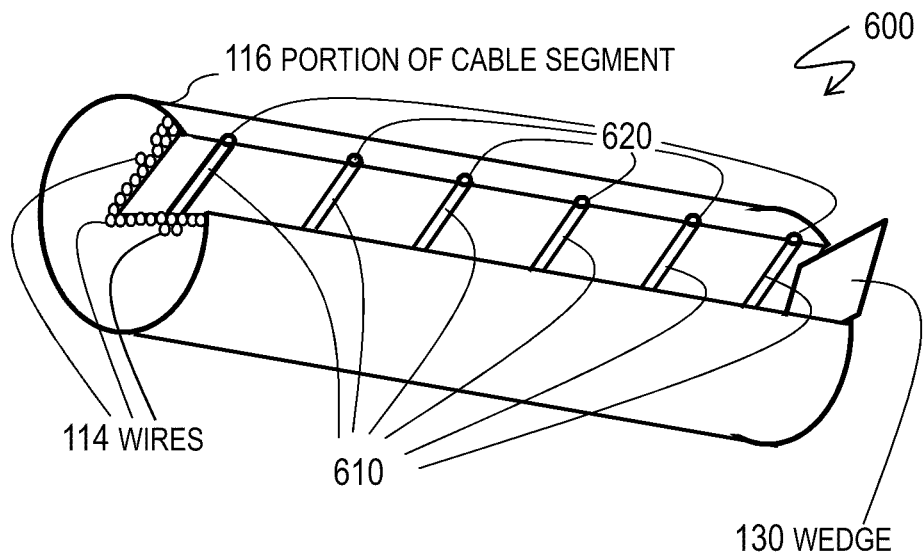
FIG. 6A is a block diagram that illustrates insertion of a series of corrosion sensors in a cable segment, according to an embodiment.

FIG. 6A is a block diagram that illustrates insertion of a series of corrosion sensors in a portion 116 of a cable segment, according to an embodiment. The portion 116 is opened for inspection using a wedge 130, as described above for FIG. 1C. The cable of portion 116 is made of a large number of individual wires 114, only some of which are depicted.

While open for inspection, corrosion sensors 610, e.g., sensors 300 or 500 or some combination, are inserted into the opened cable, e.g., at six positions along portion 116. In the illustrated embodiment, the sensor length of each inserted sensor 610 is sufficiently close to the radius of cable 110 to reach near the center and still expose the connector 620, e.g. connector 320 or connector 520, to the surface of the cable.

Figure 6B:
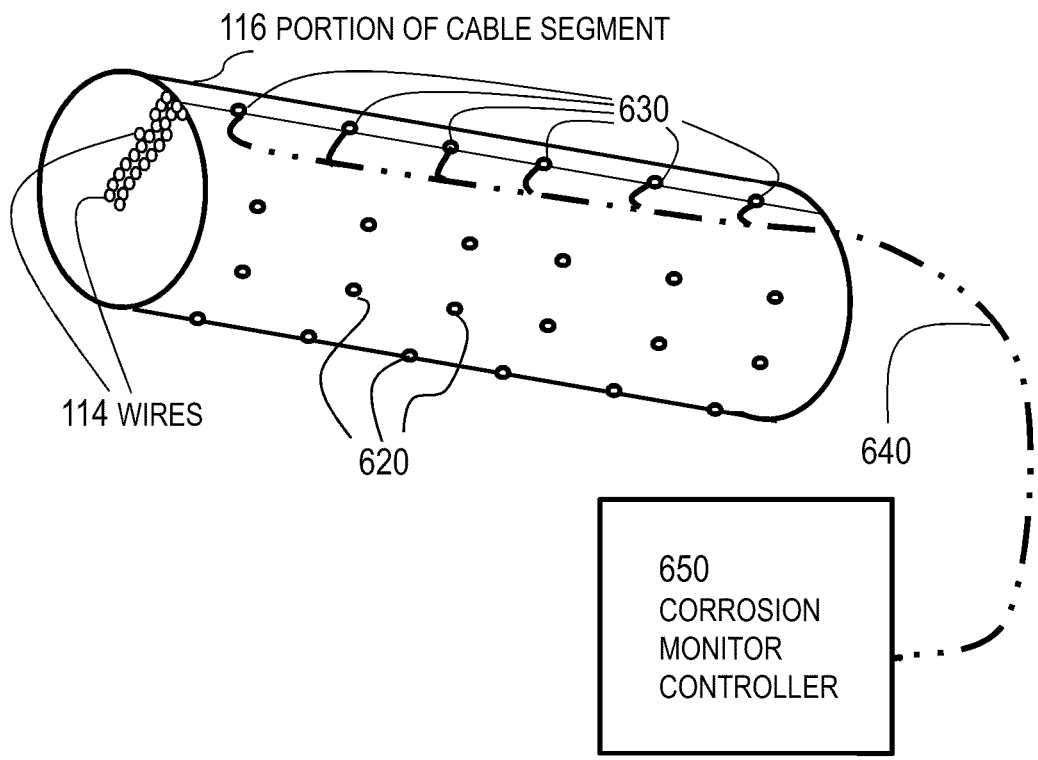
FIG. 6B is a block diagram that illustrates a corrosion monitoring system for a cable segment, according to an embodiment.

FIG. 6B is a block diagram that illustrates a corrosion monitoring system for a cable segment, according to an embodiment. This depicts the portion 116 of the cable segment after it has been inspected at eight different angles around the circumference of the cable, and a series of corrosion sensors have been inserted along each opening. Only the connectors 620 of the corrosion sensors are exposed on the surface of the cable.

The exposed connectors 620 are coupled to communication link 640 with a corrosion monitor controller 650 using couplings 630. The couplings 630 are connected to each connector 620. In some embodiments, the link 640 is a wired link, and the coupling 630 is just a plug and socket connecting each peg of connector (e.g., connector 320 or connector 520) to a different conductor in the link 640. In some embodiments, the couplings 630 are network nodes that make corrosion determinations or other measurements used for corrosion determinations and pass data packets along link 640. In some embodiments, the link 640 is a wireless link, and couplings 630 are wireless network nodes.

The corrosion monitor controller 650 controls the voltage difference between the reference electrode, if any, and the working electrode and determines the corrosion rate based on the measured current for each of several radial positions (e.g., 10 depths) within the cable, or at each of several angles (e.g., eight angles) around the circumference of the cable, or at each of several distances (e.g., six positions) along the portion of the cable, or some combination (e.g., a total of 480 corrosion rates measurements at each measurement time, such as every 3 hours). Thus, in some embodiments, a distance profile of rate of corrosion is determined with radial position within the structural cable.

In some embodiments, other sensors are included in the windows of the sensor casings depicted above, such as pH sensors, temperature sensors, pressure sensors, among others, that are each connected to one or more pegs of the connector atop the corrosion sensor.

The depicted embodiments have an important advantage over the prior art by conforming to the well-defined spacing between the individual wires in a cable. This permits the sensor to survive closure of the cable. In one embodiment, the electrodes are similar to technologies based on "linear polarization resistance" where a surrogate metal or alloy is monitored instead of the cable directly. In yet another embodiment, the corroding electrode is a small or large portion of one or more segments of the cable, thus enabling a more direct determination. Various embodiments include both "two- and three-electrode electrochemical measurements."

Existing corrosion sensors have not been built to fit within the very tight spaces of a cable bridge. Furthermore, off-the-shelf sensors use working electrode materials that are not identical to the cable materials and therefore do not directly measure bridge wire corrosion. These sensors must be correlated to bridge wire corrosion rates. The range of applicability of the correlation would be more limited than in the depicted embodiments. A thorough literature review of all the possible sensor technologies available has been done and it is concluded that there is no such sensor available. Various technologies have been reviewed, from Fiber Optic sensors to Linear Polarization Resistance, but all have some characteristics that create problems in a suspension cable application. The unique problems of the structural cable application are that the corrosion sensor has to be very small (<0.1 in) so that it can easily fit in the tight interstitial spaces between the thousands of wires that make the cable (each wire has a diameter of about 0.196 in) and that this sensor has to be able to function under a pressure of about 2,000 psi, which is induced by the cable compaction when the cable is under tension.

In some embodiments, monitoring of corrosion rates is performed at multiple positions in a cable. The actual sensors are connected to appropriate electronics and monitored with a configured computer system, such as one or more general purpose computers with software.

Figure 7:
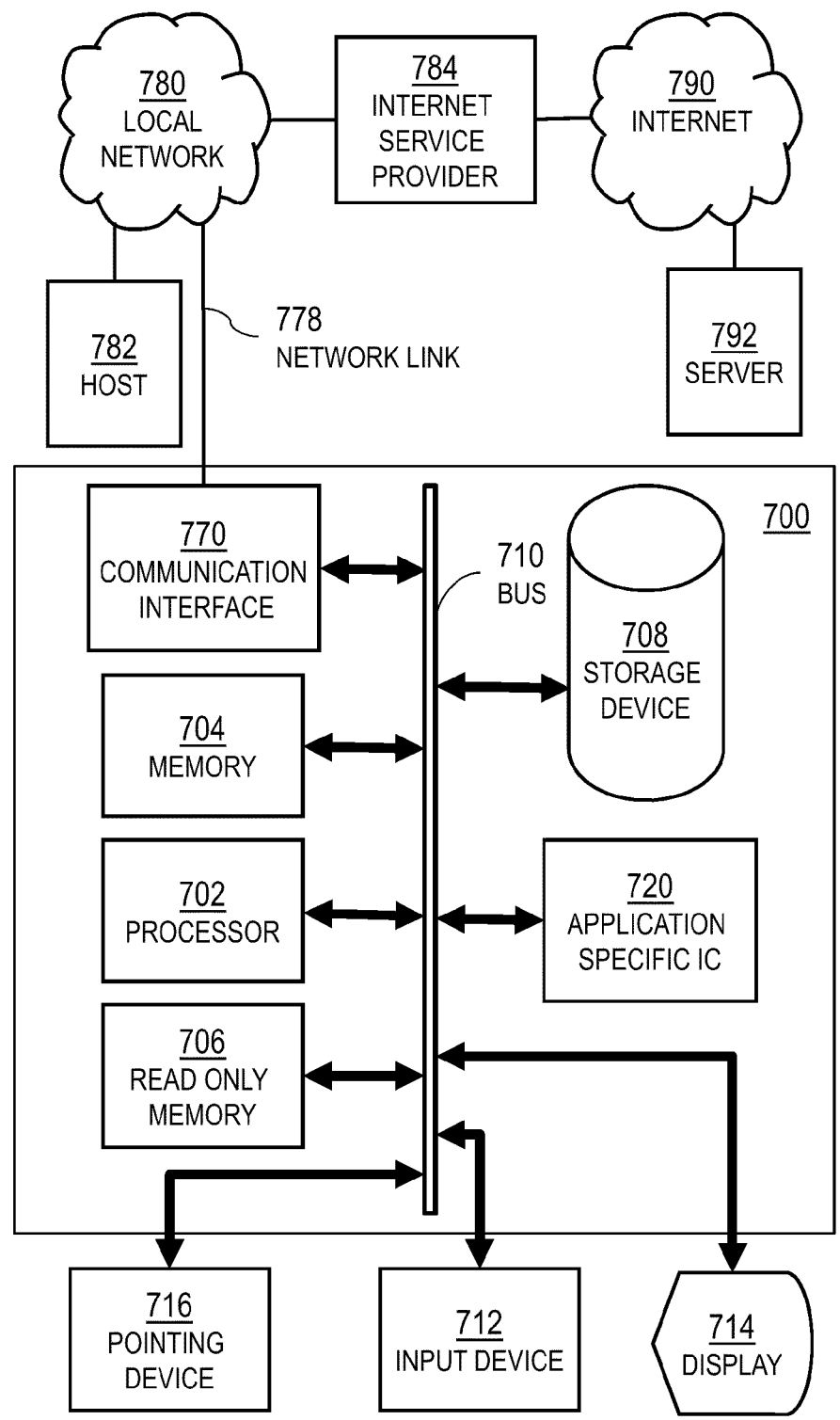
FIG. 7 is a block diagram that illustrates a computer system 700 upon which an embodiment of the invention, such as corrosion monitor controller 650, may be implemented.

FIG. 7 is a block diagram that illustrates a computer system 700 upon which an embodiment of the invention, such as corrosion monitor controller 650, may be implemented. Computer system 700 includes a communication mechanism such as a bus 710 for passing information between other internal and external components of the computer system 700. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A sequence of binary digits constitutes digital data that is used to represent a number or code for a character. A bus 710 includes many parallel conductors of information so that information is transferred quickly among devices coupled to the bus 710. One or more processors 702 for processing information are coupled with the bus 710. A processor 702 performs a set of operations on information. The set of operations include bringing information in from the bus 710 and placing information on the bus 710. The set of operations also typically include comparing two or more units of information, shifting positions of units of information, and combining two or more units of information, such as by addition or multiplication. A sequence of operations to be executed by the processor 702 constitute computer instructions.

Computer system 700 also includes a memory 704 coupled to bus 710. The memory 704, such as a random access memory (RAM) or other dynamic storage device, stores information including computer instructions. Dynamic memory allows information stored therein to be changed by the computer system 700. RAM allows a unit of information stored at a location called a memory address to be stored and retrieved independently of information at neighboring addresses. The memory 704 is also used by the processor 702 to store temporary values during execution of computer instructions. The computer system 700 also includes a read only memory (ROM) 706 or other static storage device coupled to the bus 710 for storing static information, including instructions, that is not changed by the computer system 700. Also coupled to bus 710 is a non-volatile (persistent) storage device 708, such as a magnetic disk or optical disk, for storing information, including instructions, that persists even when the computer system 700 is turned off or otherwise loses power.

Information, including instructions, is provided to the bus 710 for use by the processor from an external input device 712, such as a keyboard containing alphanumeric keys operated by a human user, or a sensor. A sensor detects conditions in its vicinity and transforms those detections into signals compatible with the signals used to represent information in computer system 700. Other external devices coupled to bus 710, used primarily for interacting with humans, include a display device 714, such as a cathode ray tube (CRT) or a liquid crystal display (LCD), for presenting images, and a pointing device 716, such as a mouse or a trackball or cursor direction keys, for controlling a position of a small cursor image presented on the display 714 and issuing commands associated with graphical elements presented on the display 714.

In the illustrated embodiment, special purpose hardware, such as an application specific integrated circuit (IC) 720, is coupled to bus 710. The special purpose hardware is configured to perform operations not performed by processor 702 quickly enough for special purposes. Examples of application specific ICs include graphics accelerator cards for generating images for display 714, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 700 also includes one or more instances of a communications interface 770 coupled to bus 710. Communication interface 770 provides a two-way communication coupling to a variety of external devices that operate with their own processors, such as printers, scanners and external disks. In general the coupling is with a network link 778 that is connected to a local network 780 to which a variety of external devices with their own processors are connected. For example, communication interface 770 may be a parallel port or a serial port or a universal serial bus (USB) port on a personal computer. In some embodiments, communications interface 770 is an integrated services digital network (ISDN) card or a digital subscriber line (DSL) card or a telephone modem that provides an information communication connection to a corresponding type of telephone line. In some embodiments, a communication interface 770 is a cable modem that converts signals on bus 710 into signals for a communication connection over a coaxial cable or into optical signals for a communication connection over a fiber optic cable. As another example, communications interface 770 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 770 sends and receives electrical, acoustic or electromagnetic signals, including infrared and optical signals, that carry information streams, such as digital data.

The term computer-readable medium is used herein to refer to any medium that participates in providing information to processor 702, including instructions for execution. Such a medium may take many forms, including, but not limited to, non-volatile media, volatile media and transmission media. Non-volatile media include, for example, optical or magnetic disks, such as storage device 708. Volatile media include, for example, dynamic memory 704. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 702, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 778 typically provides information communication through one or more networks to other devices that use or process the information. For example, network link 778 may provide a connection through local network 780 to a host computer 782 or to equipment 784 operated by an Internet Service Provider (ISP). ISP equipment 784 in turn provides data communication services through the public, world-wide packet-switching communication network of networks now commonly referred to as the Internet 790. A computer called a server 792 connected to the Internet provides a service in response to information received over the Internet. For example, server 792 provides information representing video data for presentation at display 714.

The invention is related to the use of computer system 700 for implementing the techniques described herein. According to one embodiment of the invention, those techniques are performed by computer system 700 in response to processor 702 executing one or more sequences of one or more instructions contained in memory 704. Such instructions, also called software and program code, may be read into memory 704 from another computer-readable medium such as storage device 708. Execution of the sequences of instructions contained in memory 704 causes processor 702 to perform the method steps described herein. In alternative embodiments, hardware, such as application specific integrated circuit 720, may be used in place of or in combination with software to implement the invention. Thus, embodiments of the invention are not limited to any specific combination of hardware and software.

The signals transmitted over network link 778 and other networks through communications interface 770, carry information to and from computer system 700. Computer system 700 can send and receive information, including program code, through the networks 780, 790 among others, through network link 778 and communications interface 770. In an example using the Internet 790, a server 792 transmits program code for a particular application, requested by a message sent from computer 700, through Internet 790, ISP equipment 784, local network 780 and communications interface 770. The received code may be executed by processor 702 as it is received, or may be stored in storage device 708 or other non-volatile storage for later execution, or both. In this manner, computer system 700 may obtain application program code in the form of a signal on a carrier wave.

Various forms of computer readable media may be involved in carrying one or more sequence of instructions or data or both to processor 702 for execution. For example, instructions and data may initially be carried on a magnetic disk of a remote computer such as host 782. The remote computer loads the instructions and data into its dynamic memory and sends the instructions and data over a telephone line using a modem. A modem local to the computer system 700 receives the instructions and data on a telephone line and uses an infra-red transmitter to convert the instructions and data to a signal on an infra-red a carrier wave serving as the network link 778. An infrared detector serving as communications interface 770 receives the instructions and data carried in the infrared signal and places information representing the instructions and data onto bus 710. Bus 710 carries the information to memory 704 from which processor 702 retrieves and executes the instructions using some of the data sent with the instructions. The instructions and data received in memory 704 may optionally be stored on storage device 708, either before or after execution by the processor 702.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A corrosion sensor for deployment in a structural cable of multiple wires, comprising:
a casing; and
a first counter-electrode configured to exchange electrons with ions of an electrolyte that corrodes the multiple wires of the structural cable,
wherein
the casing is shaped to mimic interstitial spaces between the multiple wires of the structural cable along a length equal to a distance more than one wire diameter of a wire of the multiple wires, and,
the first counter-electrode is embedded in the casing, is exposed in a first window of the casing, and is recessed to avoid contact with any wire of the structural cable when the sensor is deployed among the multiple wires of the structural cable.

2. A corrosion sensor as recited in claim 1, wherein the casing has a length on an order of a radius of the structural cable.

3. A corrosion sensor as recited in claim 1, further comprising a different second counter-electrode embedded in the casing, exposed in a different second window of the casing, and spaced apart along the length of the casing by a distance that is about an integer multiple of a radius of a wire in the structural cable.

4. A corrosion sensor as recited in claim 3, wherein the integer multiple is one.

5. A corrosion sensor as recited in claim 3, wherein the different second counter-electrode is configured to make an independent measurement of corrosion in the different second window of the casing, and is recessed in the different second window to avoid contact with any wire of the structural cable when the sensor is deployed among the multiple wires of the structural cable.

6. A corrosion sensor as recited in claim 1, further comprising a connector accessible when the sensor is deployed among the multiple wires of the structural cable and configured to carry an electrical current passing through the first counter-electrode.

7. A corrosion sensor as recited in claim 1, further comprising a reference electrode configured to maintain a voltage difference between the reference electrode and a working electrode that is configured to corrode in the electrolyte at a rate that is a known proportion of a corrosion rate of the multiple wires of the structural cable, wherein the reference electrode is embedded in the casing, is exposed in the first window of the casing, and is recessed to avoid contact with any wire of the structural cable when the sensor is deployed among the multiple wires of the structural cable.

8. A corrosion sensor as recited in claim 7, wherein no other electrode is exposed in the window, whereby the multiple wires of the structural cable comprise the working electrode.

9. A corrosion sensor as recited in claim 7, further comprising the working electrode wherein the working electrode is embedded in the casing, is exposed in the first window of the casing, and is recessed to avoid contact with any wire of the structural cable when the sensor is deployed among the multiple wires of the structural cable.

10. A corrosion sensor as recited in claim 1, wherein the casing is made of hard rubber that compresses less than about ten percent under pressures up to about 2000 pounds per square inch.

11. A corrosion sensor as recited in claim 1, wherein no other electrode is exposed in the first window, whereby the multiple wires of the structural cable comprise a working electrode that corrodes in the electrolyte.

* * * * *